United States Patent
Ukhanov et al.

(10) Patent No.: US 12,072,351 B1
(45) Date of Patent: Aug. 27, 2024

(54) INTEGRATED III-V/SILICON ATOMIC FORCE MICROSCOPY ACTIVE OPTICAL PROBE

(71) Applicants: Alexander A. Ukhanov, Albuquerque, NM (US); Gennady A Smolyakov, Albuquerque, NM (US); Fei Hung Chu, Albuquerque, NM (US)

(72) Inventors: Alexander A. Ukhanov, Albuquerque, NM (US); Gennady A Smolyakov, Albuquerque, NM (US); Fei Hung Chu, Albuquerque, NM (US)

(73) Assignee: ACTOPROBE LLC, Albuquerque, NM (US)

(*) Notice: Subject to any disclaimer, the term of this patent is extended or adjusted under 35 U.S.C. 154(b) by 871 days.

(21) Appl. No.: 16/954,000

(22) Filed: Nov. 20, 2020

Related U.S. Application Data

(60) Provisional application No. 62/945,130, filed on Dec. 7, 2019.

(51) Int. Cl.
| | |
|---|---|
| *G01Q 60/06* | (2010.01) |
| *C12Q 1/6869* | (2018.01) |
| *G01N 21/65* | (2006.01) |
| *H01S 5/06* | (2006.01) |
| *H01S 5/34* | (2006.01) |
| *H01S 5/343* | (2006.01) |

(52) U.S. Cl.
 CPC .......... *G01Q 60/06* (2013.01); *C12Q 1/6869* (2013.01); *G01N 21/65* (2013.01); *H01S 5/0601* (2013.01); *H01S 5/3402* (2013.01); *H01S 5/343* (2013.01)

(58) Field of Classification Search
 CPC ...... G01Q 60/06; C12Q 1/6869; G01N 21/65; H01S 5/0601; H01S 5/3402; H01S 5/343
 USPC .......................................................... 850/24
 See application file for complete search history.

(56) References Cited

U.S. PATENT DOCUMENTS

| | | | | |
|---|---|---|---|---|
| 5,982,009 | A * | 11/1999 | Hong | G01Q 20/04 850/52 |
| 6,882,429 | B1 * | 4/2005 | Weitekamp | G02B 6/3504 356/482 |
| 9,482,691 | B1 * | 11/2016 | Ukhanov | G01Q 60/06 |
| 11,016,119 | B1 * | 5/2021 | Ukhanov | G01Q 70/14 |
| 2009/0073432 | A1 * | 3/2009 | Jalali | G01N 21/65 356/301 |
| 2013/0176563 | A1 * | 7/2013 | Ozawa | G01N 33/48721 356/301 |

* cited by examiner

*Primary Examiner* — Michael Maskell

(57) ABSTRACT

A new integrated III-V/silicon Atomic Force Microscopy (AFM) active optical probe integrates a III-V semiconductor laser source and a silicon cantilever AFM probe into a robust easy-to-use single III-V/silicon chip to enable AFM measurements, optical imaging, and spectroscopy at the nanoscale.

14 Claims, 4 Drawing Sheets

INTEGRATED III-V/SILICON ATOMIC FORCE MICROSCOPY ACTIVE OPTICAL PROBE

CROSS REFERENCE TO RELATED APPLICATIONS

This application claims benefit and priority of U.S. provisional application Ser. No. 62/945,130 filed Dec. 7, 2019, the entire disclosure of which is incorporated herein by reference.

FIELD OF THE INVENTION

The present invention relates to atomic force microscopy (AFM) and near-field optical microscopy probes and, in particular, to an integrated III-V/silicon AFM active optical probe capable of performing conventional AFM measurements, near-field optical imaging, and optical spectroscopy at the nanoscale.

BACKGROUND OF THE INVENTION

While science and technology greatly benefit from Atomic Force Microscopy (AFM) in surface characterization, optical imaging at the nanoscale, such as Near-Field Scanning Optical Microscopy (NSOM) and nanospectroscopy (e.g., Tip-Enhanced Raman Spectroscopy (TERS), Tip-Enhanced FTIR Spectroscopy (TEFS), and Photothermal IR Spectroscopy) lags far behind. Current AFM technology obtains information about the mechanical properties only. Hybrid AFM equipped with a specialized far-field optical microscope or NSOM are normally used to probe the optical properties of the sample. These techniques have limited applications since they are expensive and difficult to use, and produce poor data quality at single-molecule or submolecular scale.

A. GaAs-Based AFM Active Optical Probes Vs. Integrated III-V/Silicon AFM Active Optical Probes Previously, we proposed a novel class of active probes for combined AFM/NSOM/TERS measurements. AFM active optical probes (AAOPs) are near-field optical probes that fit onto a conventional AFM and allow one to combine the high lateral resolution of AFM with near-field optical measurements. AAOPs are considered to be a cost-effective alternative to expensive NSOMs and to various hybrids of AFMs equipped with specialized far-field optical microscopes.

We pursued the concept of AAOP fabricated entirely from GaAs-based or similar lattice-matched semiconductor laser materials, including the semiconductor laser source, the photodetector, the cantilever with the tip on its end, and the probe base, all monolithically integrated into a semiconductor chip for combined AFM/NSOM/TERS measurements [1]. As important as it is for establishing the general concept of AAOP, this approach is not the most economical in utilizing relatively expensive III/V material, which makes the final product rather costly. At the same time, in terms of their mechanical properties, GaAs-based cantilever AFM probes are typically inferior to standard silicon cantilever AFM probes. To take full advantage of both the III/V semiconductor laser technology and the established silicon microfabrication techniques of the standard technology of AFM tip/cantilever manufacturing, we propose a novel concept of integrated III-V/silicon AAOP.

B. Ultrafast Pulsed AAOP Technology

In addition to unique imaging/spectroscopy capabilities, the integrated III-V/silicon AAOP technology can be naturally extended to ultrafast pulsed (UFP) AAOP technology that provides an exciting opportunity for obtaining both space- and time-resolved chemical information by way of ultrafast TERS measurements, and, most importantly, extends the AAOP technology into the visible optical range by using nonlinear optical effects such as two-photon or three-photon excitation and detection. Integration of an external pulsed excitation source with TERS for time-resolved spectroscopy is very challenging [2]. In contrast, the UFP AAOP technology naturally provides the ultrafast time-resolved spectroscopy capability. The integrated semiconductor laser sources with specialized gain media, such as InAs quantum dots, offer mode-locking capabilities for sub-picosecond pulse generation [3, 4]. Integrating the ultrafast pulsed laser source into a silicon cantilever AFM probe will allow probing the site-specific dynamic response of chemical systems. This imaging technique combining molecular scale spatial resolution and ultrafast temporal resolution can be applied, e.g., for exploring energy flow, molecular dynamics, breakage/formation of chemical bonds or conformational changes in nanoscale systems, and so on.

UFP AAOP will also be of particular interest for tip-enhanced hyper-Raman spectroscopy (TEHRS) of biological samples. Hyper-Raman scattering (HRS) is a two-photon-excited Raman scattering process that provides several advantages over one-photon excitation [5-7]. In an HRS experiment, the excitation with light in the near infrared, convenient for biological samples, is combined with the desirable detection in the visible spectral range. Besides, the two-photon excitation is favorable for microscopic applications due to the increased penetration depth and limited probed volume [8], resulting in an improved resolution for imaging. Last but not least, TEHRS benefits even to a greater extent from the high local optical fields than normal Raman scattering does in the case of TERS, because of its nonlinear dependence on the enhanced excitation field. TEHRS, therefore, has the potential to be much more sensitive than TERS and to provide better insight into the structure and interaction of molecules on surfaces [9]. As a nonlinear incoherent Raman process, HRS is an extremely weak effect with scattering cross-sections 35 orders of magnitude smaller than cross-sections of "normal" (one-photon-excited) Raman scattering. To be observed, the effect requires very high excitation intensities provided in high-energy laser pulses or by tightly focused femtosecond or picosecond mode-locked lasers [11]. In TEHRS, however, the strong field enhancement can compensate for the extremely small cross-section of HRS and allows the measurement of TEHRS spectra at excitation intensities of $10^6$ to $10^7$ W/cm$^2$ [12], conditions that can be easily achieved with mode-locked picosecond lasers under focusing conditions of UFP AAOP.

C. AAOP Technology for Rapid Virus Detection/Identification and DNA/RNA Sequencing Preliminary analysis shows that the AAOP technology is extremely attractive for rapid virus detection/identification and DNA sequencing. Rapid diagnosis of virus infection is critical for controlling viral spread in its early stage. Developing simple, fast, and economical virus detection techniques is crucial for early viral infection identification, early treatment, and increased likelihood of patient survival. The mainstream methods in virus surveillance such as fluorescent antibody assays, enzyme-linked immunosorbent assay (ELISA), and polymerase chain reaction (PCR) are based on the detection of viral antigens and/or nucleic acids of viruses. Most of these technologies suffer from complex procedures, poor sensitivity, as well as time and cost ineffectiveness. Collected samples are subjected to a series of time-consuming steps, such as ultracentrifugation and cell culture, to enrich virus particles or amplify virus titers. The low virus titer in most samples leads to sequence reads dominated by host genetic material rather than by viral pathogens. Various enrichment methods, including virus culture and genome amplification, often introduce artificial variants in the sequence reads and are impractical when samples are time sensitive. In addition, the requirement for predefined labels such as target virus-specific antibodies limits use of the conventional methods for the rapid identification of newly emerging viruses.

Viruses possess surface proteins and lipids that can generate distinctive Raman signals, and Raman spectroscopy has been identified as a suitable and effective tool to examine a single live cell for virus infection without the need for labeling and the time it takes to do so [13-20]. The obvious advantage of the Raman technique over conventional immunostaining and genetic tests for detection of human infectious viruses is that it does not require any genetic or proteomic information about the virus in advance. Tip-enhanced Raman spectroscopy (TERS) [13, 15, 21], surface-enhanced Raman spectroscopy (SERS) [14, 16, 20, 22-28], and volume-enhanced Raman spectroscopy (VERS) have been applied to virus detection and identification. However, purification of biological samples and massive virus culture amplification were still needed for reliable virus detection and identification. Raman techniques capable of single-particle detection and identification of viruses, whose typical size is sub-100 nm, are in high demand. A unique submolecular resolution of the AAOP technology can be used for rapid and label-free optical detection and identification of viruses directly from clinical samples without their preliminary purification or enrichment.

DNA sequencing is a bottleneck of modern genomics and bioinformatics. Therefore, alternative methods of DNA and RNA sequencing are highly desired. During the last two decades, some attempts have been made to read DNA and RNA nucleotide sequences using TERS. Unfortunately, biological molecules such as DNA have much lower Raman scattering cross sections than the resonant dyes commonly investigated in single-molecule TERS, making their detection challenging. The temptation to simply raise the excitation laser power to generate more Raman scattering leads to decomposition. If one works at sufficiently low laser power, long integration times are required, which leads to slow imaging rates and problems with drift. There have been claims of nanometer or even subnanometer spatial resolution with ambient TERS. The Deckert group attempted to reach <1 nm spatial resolution using TERS for sequencing specifically designed single-stranded DNA [29]. However, such high-resolution TERS proved extremely difficult to reproduce. At present, there is only one other report in the literature where a silver tip was scanned along a single-stranded DNA to collect TERS signals with a step of 0.5 nm, comparable to the bond length between two adjacent DNA bases [30]. A unique single-molecule sensitivity and spatial resolution of the AAOP technology can be used for rapid sequencing single- and double-stranded DNA and RNA.

SUMMARY OF THE INVENTION

The innovation is accomplished by integrating a III-V semiconductor laser source and a photodetector monolithically into a silicon cantilever AFM probe. Because the production of individual probes is tedious and not easily reproducible, it is desirable to fabricate standardized probes in large batches with highly reproducible properties (e.g., aperture size, shape, and, hence, transmission) using established silicon microfabrication techniques of the standard AFM cantilever technology. Delivery of light to the optical probe tip is an obvious problem in such a concept due to the absence of Si-based laser sources, and, as a consequence, most developments deal with the microfabrication of aperture tips only that can then be bonded to fibers or integrated into a cantilever. Fabrication of passive cantilever probes has been attempted by integrating a waveguide into the cantilever. Such cantilever probes are classified as 'passive' probes because they influence the propagation of light but not its generation. Silicon microstructures are in principle compatible with III-V semiconductor laser functionality and fabrication of active light-emitting cantilever probes can be attempted by integrating a III-V semiconductor laser source directly into the cantilever of a silicon AFM probe or into its base. An 'active' probe is the one that is itself a subwavelength source of light driven by an electric current. We propose a special intracavity design for the AAOP where the gold-coated silicon tip itself acts also as the output laser mirror. In that way, the probe tip is part of the laser cavity that is immediately supplied with intracavity high-intensity laser light. The proposed design takes advantage of the high-intensity intracavity laser light supplied through the tip and delivered directly to the tip apex. The dramatically enhanced coupling of excitation light into the tip apex in the near-field has the potential to solve the main fundamental problem of NSOM, namely, its low sensitivity (low signal-to-noise ratio) and will result in at least ten-fold improvement in TERS resolution and measurement time.

These and other advantages of the present invention will become more readily apparent from the following detailed description taken with the following drawings.

DETAILED DESCRIPTION OF THE INVENTION

The silicon integrated AAOP concept is based on integrating a III-V semiconductor laser source monolithically into a silicon cantilever AFM probe. We propose a special intracavity design for the AAOP where the gold-coated silicon tip itself acts also as the output laser mirror. In that way, the probe tip is part of the laser cavity that is immediately supplied with intracavity high-intensity laser light. This design takes advantage of the high-intensity intracavity laser light supplied through the tip and delivered directly to the tip apex. The dramatically enhanced coupling of excitation light into the tip apex in the near-field is expected to solve the main fundamental problem of NSOM, namely, its low sensitivity.

The most established approach for integration of III-V semiconductor lasers on silicon is heterogenous laser integration through evanescent coupling with silicon-on-insulator (SOI) waveguide based on wafer bonding techniques [31, 32]. The proposed special intracavity design of the AAOP, however, is not entirely compatible with this III-V silicon integration approach, as the thickness of the silicon waveguide layer is limited to less than ~ 500 nm [31]. We find an alternative III-V silicon integration approach, developed by Skorpios Technologies, to be much more appropriate for our purposes [33]. The approach is based on metal bonding the III-V gain medium section to the SOI silicon substrate for direct optical coupling (edge- or butt coupling) between the III-V gain section and the silicon layer of the SOI waveguide. As distinct from other configurations, the III-V gain section is planar with the silicon waveguide layer, providing high efficiency optical coupling.

Some preferred embodiments of the invention will be described below in detail based on the drawings.

Embodiment 1

Figure 1:
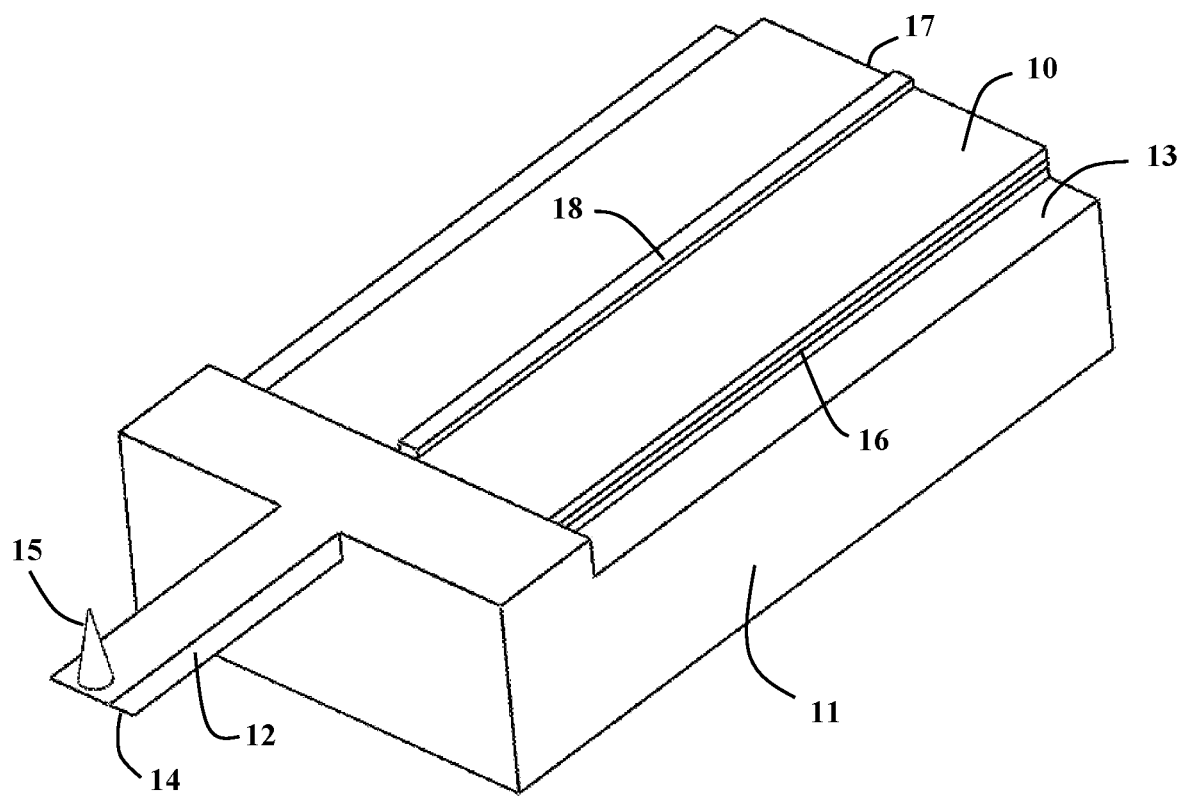
FIG. 1 is a three-dimensional illustration of the integrated III-V/silicon AAOP concept according to Embodiment 1 of the invention.

In an illustrative embodiment of the present invention, a III-V semiconductor laser chip 10 is buried in the base 11 of a commercially available silicon AFM probe in front of the cantilever 12 and aligned with the cantilever to efficiently couple the laser light into the cantilever by way of butt (edge) coupling (FIG. 1). An epitaxial III-V gain material piece is metal-bonded within pre-etched pit receptor site 13 inside the base 11 of the silicon AFM probe and then processed into the laser chip. The cantilever acts as an optical waveguide with silicon core and air claddings. In this approach, the III-V gain section is planar with the silicon cantilever/waveguide, providing high efficiency direct optical coupling between the two regions. The light is then redirected vertically from the silicon waveguide into the probe tip using a folding mirror 14. The gold-coated tip 15 acts as an output laser mirror in the special intracavity design of the AAOP. The light reflected from the gold-coated tip is coupled back into the silicon cantilever/waveguide 12 and, eventually in the laser chip active region 16. This light feedback mechanism has to be sufficiently strong to make sure that the probe tip 15 is supplied with intracavity high-intensity laser light.

Two different modes of light propagation are inherent in the compound cavity of this specific optical design of AAOP. One is light propagation in the silicon cantilever/waveguide as a confined optical waveguide mode. The other is free propagation of light with no intensity confinement mechanism provided. The latter happens after the waveguide mode hits the silicon/air interface of the folding mirror 14 and gets redirected vertically towards the probe tip 15. To prevent strong divergence of the waveguide mode light after it escapes the silicon optical waveguide and starts propagating freely towards the probe tip, the silicon cantilever/waveguide 12 should be of sufficient, several microns, thickness. The silicon integrated III-V laser chip 10 will be fabricated from a specially designed semiconductor laser epitaxial structure with significantly improved divergence along the fast axis (across the epitaxial layers). This special design of the laser epitaxial structure is expected to radically improve coupling of the laser light into the silicon cantilever/waveguide 12 and the feedback from the gold-coated tip 15 into the silicon waveguide/cantilever and, eventually, into the laser active region 16. In particular, the longitudinal photonic band crystal (PBC) waveguide design will be used [34-38]. The longitudinal PBC design demonstrates a vertical divergence angle less than 10 degrees full width at half maximum (FWHM) [36].

After the bonding of the III-V epitaxial material, an air gap remains between the gain section and the crystalline silicon waveguide. To suppress undesirable reflections between the gain waveguide and the silicon waveguide, the air gap is eliminated by reconstructing the silicon layer in the gap. The refractive indices of III-V material and silicon are very close, reducing the reflection coefficient to $10^{-3}$-$10^{-4}$ at the III-V/silicon interface and thus making the output laser chip facet practically nonexistent. The back facet of the laser chip 17 can be gold coated to increase the quality factor of the effective three-mirror laser cavity formed by the gold-coated back facet 17 of the III-V laser chip, the folding mirror 14 in the end of the silicon cantilever 12, and the gold-coated probe tip 15. This accomplishes the special intracavity design of the AAOP. The optical gain in the silicon integrated III-V laser chip can be provided by bulk active region, by single or multiple quantum well active layers, or by a single or multiple layers of quantum dots in the active region 16 of the III-V epitaxial structure. The epitaxial structure of the III-V laser chip can be that of quantum cascade semiconductor laser. The semiconductor laser chip can have a ridge waveguide structure 18 for lateral mode confinement.

In the intracavity design of the AAOP, the terminal voltage on the III/V laser chip is expected to be extremely sensitive to any optical feedback into the laser cavity from the nanosized volume of a sample located under the tip apex, which can be used for signal detection, thus realizing the principle of intracavity light detection.

Embodiment 2

Combining AFM probe with ultrafast near-field light source allows one to simultaneously achieve single-molecule spatial resolution and subpicosecond time resolution. The best way to achieve ultrafast laser pulse generation is to employ a passive mode-locking technique by dividing the laser cavity into two sections—a longer gain section and a shorter saturable absorber section. The gain section is forward biased, while the saturable absorber section is reverse biased. Electrical isolation between these two sections is achieved by using shallow dry etching to remove the heavily doped layers in the gap region.

Figure 2:
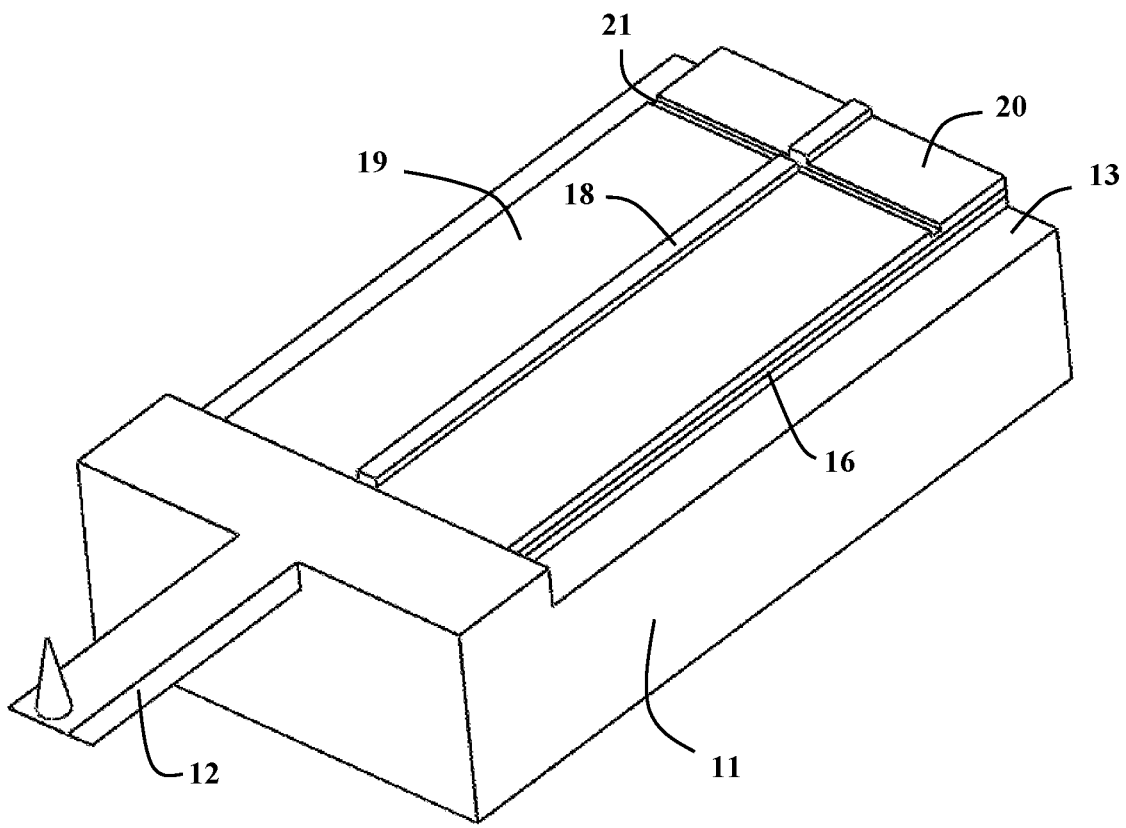
FIG. 2 is a three-dimensional illustration of the integrated III-V/silicon AAOP concept according to Embodiment 2 of the invention.

Another illustrative embodiment of the present invention is similar to Embodiment 1, except that the III-V chip is a two-section device divided into electrically isolated gain section 19 and saturable absorber section 20 to allow ultrafast pulse generation capability (FIG. 2). As described in Embodiment 1, the epitaxial III-V gain material piece is metal-bonded to the silicon substrate within the pre-etched pit receptor site 13 inside the base 11 of the probe and then processed into the two-section laser chip. Electrical isolation between the gain and absorber sections is achieved by using shallow dry etching to remove any heavily doped layers in the gap region 21 that does not penetrate the active region 16. The cantilever 12 acts as an optical waveguide with silicon core and air claddings. In this approach, the III-V gain section is planar with the silicon cantilever/waveguide, providing high efficiency direct optical coupling between the two regions.

The III-V saturable absorber section 20 can be used as an efficient intracavity high-speed photodetector (PD) [39, 40]. The voltages of proper polarity and magnitude are applied to the gain and absorber/PD sections to achieve mode locking and intracavity light detection.

The optical gain in the silicon integrated III-V laser chip can be provided by bulk active region, by single or multiple quantum well active layers, or by a single or multiple layers of quantum dots in the active region 16 of the III-V epitaxial structure. The epitaxial structure of the III-V laser chip can be that of quantum cascade semiconductor laser. The semiconductor laser chip can have a ridge waveguide structure 18 for lateral mode confinement.

Embodiment 3

In yet another illustrative embodiment of the present invention, the silicon AFM probes with integrated III-V laser sources are mass-produced from a specially designed silicon-on-insulator (SOI) wafer. The design is similar to the one described in the previous embodiments, except that silicon ridge or rib waveguide is designed and fabricated on the base of the probe and on the cantilever to deliver the laser light to the probe tip.

Figure 3:
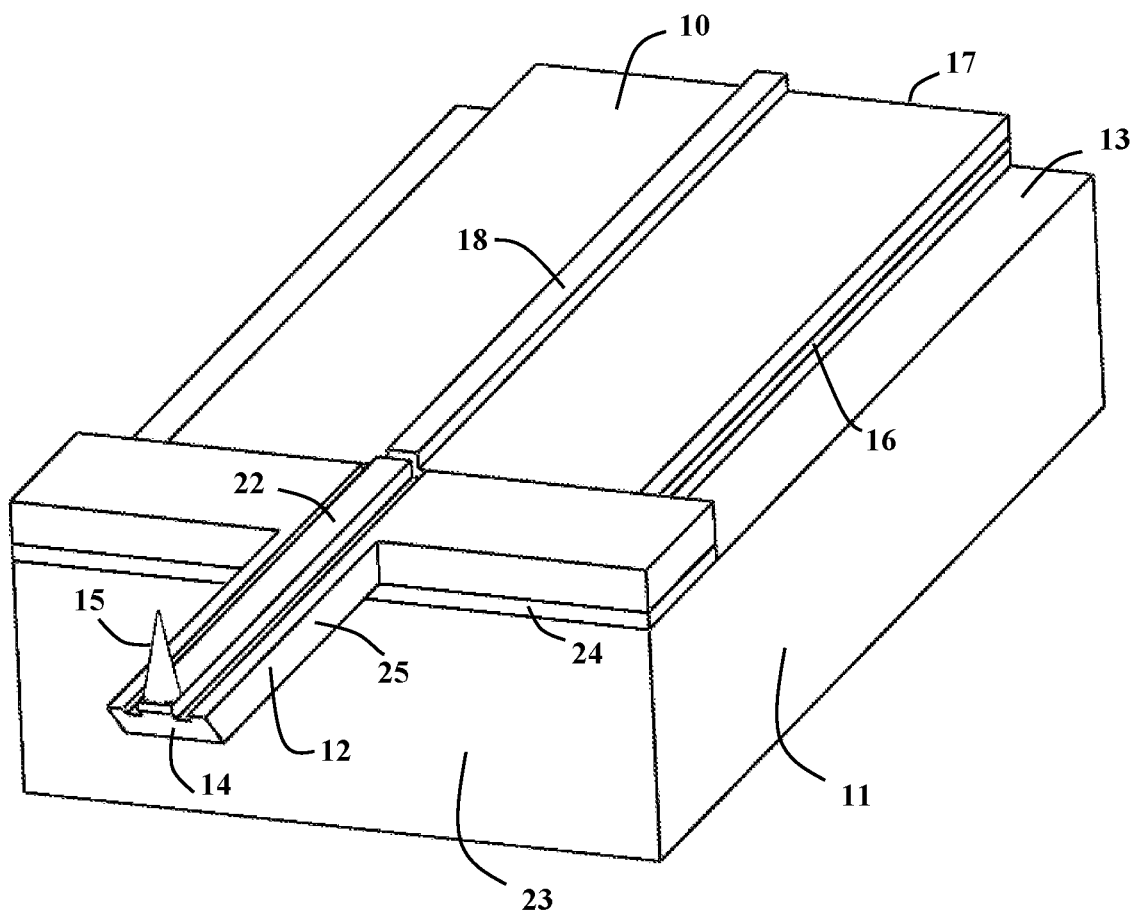
FIG. 3 is a three-dimensional illustration of the integrated III-V/silicon AAOP concept according to Embodiment 3 of the invention.

The integrated III-V/silicon AFM active optical probe is shown in FIG. 3. The base of the probe 11, the cantilever 12, the tip 15, and the SOI ridge waveguide 22 are structured in the first stage of fabrication process from a special SOI wafer. The unprocessed SOI wafer consists of a thick silicon substrate layer 23, an isolating $SO_2$ layer 24, and a silicon waveguide layer 25. The silicon waveguide layer of the unprocessed SOI wafer is sufficiently thick (~10 μm) to allow fabrication of a tip sitting on top of a relatively thick (~5 μm) silicon ridge waveguide extending from the probe base onto the cantilever. An epitaxial III-V gain material is embedded in the base of the probe in such a way that its active layer 16 is planar and properly aligned with the silicon ridge waveguide 22 to efficiently couple the laser light into the ridge waveguide by way of butt (edge) coupling. The epitaxial III-V gain material piece is metal-bonded to the silicon substrate 23 within the pre-etched pit receptor site 13 inside the base 11 of the probe and then processed into the laser chip 10 that has a ridge-waveguide structure 18 properly aligned with the silicon ridge waveguide 22 to efficiently couple the laser light into the silicon ridge waveguide by way of butt (edge) coupling. The light is delivered to the end of the cantilever 12 where it is redirected vertically from the silicon ridge waveguide 22 into the probe tip 15 using a folding mirror 14. The gold-coated tip 15 acts as an output laser mirror in the special intracavity design of the AAOP. The light reflected from the gold-coated tip 15 is coupled back into the silicon waveguide 22 and, eventually in the laser chip active region 16. This light feedback mechanism has to be sufficiently strong to make sure that the probe tip is supplied with intracavity high-intensity laser light.

To prevent strong divergence of the waveguide mode light after it escapes the silicon optical waveguide 22 and starts propagating freely towards the probe tip 15, the silicon waveguide 22 should be of sufficient, several microns, thickness. The silicon integrated III-V laser chip 10 will be fabricated from a specially designed semiconductor laser epitaxial structure with significantly improved divergence along the fast axis (across the epitaxial layers), as described above in Embodiment 1. This special design of the laser epitaxial structure is expected to radically improve coupling of the laser light into the silicon waveguide 22 and the feedback from the gold-coated tip 15 into the silicon waveguide 22 and, eventually, into the laser active region 16.

After the bonding of the III-V epitaxial material, an air gap remains between the gain section and the crystalline silicon waveguide. To suppress undesirable reflections between the gain waveguide and the silicon waveguide, the air gap is eliminated by reconstructing the buried oxide layer in the gap and building an amorphous silicon waveguide with identical cross section to that of the crystalline silicon waveguide. The refractive indices of III-V material and silicon are very close, reducing the reflection coefficient to $10^{-3}$-$10^{-4}$ at the III-V/silicon interface and thus making the output laser chip facet practically nonexistent, just as it is required for the special intracavity design of the AAOP. As described in [33], after bonding, removing the III/V substrate, and reconstructing the silicon waveguide structure in the air gap, the ridge waveguide 18 is defined throughout the coupling region and the III-V material, such that it is inherently aligned to the original SOI waveguide 22. Finally, silicon dioxide is deposited, hermetically sealing the laser. The device wiring can be realized through the highly conducting silicon substrate 23 (bottom contact) and through metal vias (top contact). The back facet 17 of the laser chip can be gold coated to increase the quality factor of the effective three-mirror laser cavity formed by the gold-coated back facet 17 of the III-V laser chip, the folding mirror 14 in the end of the silicon cantilever 12, and the gold-coated probe tip 15.

The optical gain in the silicon integrated III-V laser chip can be provided by bulk active region, by single or multiple quantum well active layers, or by a single or multiple layers of quantum dots in the active region 16 of the III-V epitaxial structure. The epitaxial structure of the III-V laser chip can be that of quantum cascade semiconductor laser.

The SOI waveguide can also be implemented as rib SOI waveguide.

In the intracavity design of the AAOP, the terminal voltage on the III/V laser chip is expected to be extremely sensitive to any optical feedback into the laser cavity from the nanosized volume of a sample located under the tip apex, which can be used for signal detection, thus realizing the principle of intracavity light detection.

The main advantage of this approach is good thermal conductivity through the silicon substrate. We note also that alignment between the III/V layers and the silicon waveguide is much easier in our particular case due to intentionally increased waveguide dimensions for both.

Embodiment 4

Figure 4:
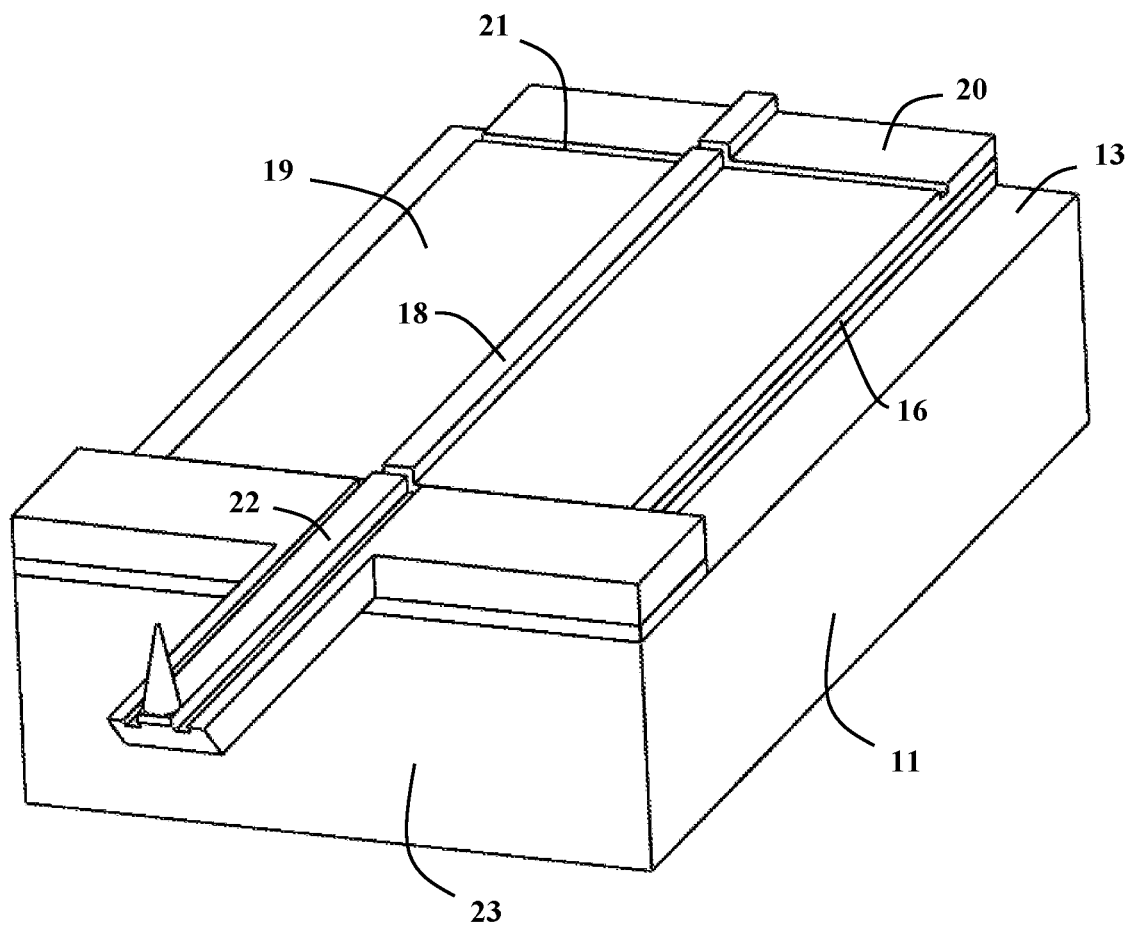
FIG. 4 is a three-dimensional illustration of the integrated III-V/silicon AAOP concept according to Embodiment 4 of the invention.

Yet another illustrative embodiment of the present invention is similar to Embodiment 3, except that the III-V chip is a two-section device divided into electrically isolated gain section 19 and saturable absorber section 20 to allow ultrafast pulse generation capability (FIG. 4). As described in Embodiment 3, the epitaxial III-V gain material piece is metal-bonded p-side down to the silicon substrate 23 within the pre-etched pit receptor site 13 inside the base 11 of the probe and then processed into the two-section laser chip. After bonding, removing the III/V substrate, and reconstructing the silicon waveguide structure in the air gap, the ridge waveguide 18 is defined throughout the coupling region and the III-V material, such that it is inherently aligned to the original SOI waveguide 22. Electrical isolation between the gain and absorber sections is achieved by using shallow dry etching to remove any heavily doped layers in the gap region 21 that does not penetrate the active region.

Finally, silicon dioxide is deposited, hermetically sealing the laser. The device wiring can be realized through the highly conducting silicon substrate 23 (common bottom contact) and through metal vias (top contacts to independently contact the gain and saturable absorber sections).

The optical gain in the silicon integrated III-V laser chip can be provided by bulk active region, by single or multiple quantum well active layers, or by a single or multiple layers of quantum dots in the active region 16 of the III-V epitaxial structure. The epitaxial structure of the III-V laser chip can be that of quantum cascade semiconductor laser.

The III-V saturable absorber section 20 can be used as an efficient intracavity high-speed photodetector (PD). The voltages of proper polarity and magnitude are applied to the gain and absorber/PD sections to achieve mode locking and intracavity light detection.

Embodiment 5

In yet another illustrative embodiment of the present invention, the III-V gain chip is evanescently coupled with the silicon ridge or rib waveguide fabricated on the probe base and on the cantilever as described in Embodiment 3 and Embodiment 4. This can be done using flip chip bonding or epitaxial layer transfer (printing transfer) [31].

Method Embodiment for Virus Detection Using AAOP

A method embodiment of the invention provides a method of virus detection and identification using AAOP. The method embodiment includes the steps of providing an integrated III-V/silicon atomic force microscopy active optical probe comprising a III-V semiconductor laser chip providing a gain medium section, a silicon cantilever atomic force microscopy probe, and a photodetector, all monolithically integrated into a single III-V/silicon chip; mounting the integrated III-V/silicon atomic force microscopy active optical probe on an atomic force microscopy system; applying a direct current bias to the semiconductor laser chip such that the laser light power delivered to the tip apex of the probe is sufficient to do tip-enhanced Raman scattering or near-field scanning optical microscopy measurements; applying reverse voltage bias to the photodetector; and performing a tip-enhanced Raman scattering measurement or near-field scanning optical microscopy measurement on a single virus particle. In one method embodiment, the III-V semiconductor laser chip is a two-section device divided into electrically isolated gain section and saturable absorber section to allow ultrafast pulse generation, and the saturable absorber section is used as a photodetector for intracavity light detection in the near-field scanning optical microscopy measurement.

Method Embodiment for DNA/RNA Sequencing Using AAOP

A method embodiment of the invention provides a method of DNA/RNA sequencing using AAOP. The method embodiment includes the steps of providing an integrated III-V/silicon atomic force microscopy active optical probe comprising a III-V semiconductor laser chip providing a gain medium section, a silicon cantilever atomic force microscopy probe, and a photodetector, all monolithically integrated into a single III-V/silicon chip; mounting the integrated III-V/silicon atomic force microscopy active optical probe on an atomic force microscopy system; applying a direct current bias to the semiconductor laser chip such that the laser light power delivered to the tip apex of the probe is sufficient to do tip-enhanced Raman scattering or near-field scanning optical microscopy measurements; applying reverse voltage bias to the photodetector; and performing a tip-enhanced Raman scattering measurement or near-field scanning optical microscopy measurement on a single-stranded DNA, double-stranded DNA, or RNA molecules, stretched and attached to a fixed surface at both ends, by way of base-to-base readout necessary for DNA/RNA sequencing.

In all embodiments, the silicon cantilever atomic force microscopy probe used for integration with the III/V laser chip can alternatively be a silicon nitride cantilever atomic force microscopy probe fabricated, if necessary, from a specially designed silicon-nitride-on-insulator (SiNOI) wafer.

Although certain embodiments of the invention have been described in detail herein, those skilled in the art will appreciate that modifications and changes can be made therein with the scope of the invention as set forth in the appended claims.

REFERENCES CITED

[1] A. A. Ukhanov, G. A. Smolyakov, "Atomic force microscopy active optical probe", Patent No. U.S. Pat. No. 9,482,691, issued Nov. 1, 2016.
[2] J. M. Klingsporn, M. D. Sonntag, T. Seideman, R. P. Van Duyne, "Tip-enhanced Raman spectroscopy with picosecond pulses", J. Phys. Chem. Lett. 5 (#1), pp. 106-110, 2014.
[3] X. Huang, A. Stintz, H. Li, L. F. Lester, J. Cheng, and K. J. Malloy, "Passive mode-locking in 1.3 µm two-section InAs quantum dot lasers," Appl. Phys. Lett. 78(#19), pp. 2825-2827, 2001.
[4] E. U. Rafailov, M. A. Cataluna, W. Sibbett, "Mode-locked quantum-dot lasers", Nature Photonics 1, pp. 395-401, 2007.
[5] J. Kneipp, H. Kneipp, K. Kneipp, "Two-photon vibrational spectroscopy for biosciences based on surface-enhanced hyper-Raman scattering", Proc. Natl. Acad. Sci. USA 103(#46), pp. 17149-17153, 2006.
[6] F. Madzharova, Z. Heiner, J. Kneipp, "Surface enhanced hyper Raman scattering (SEHRS) and its applications", Chem. Soc. Rev. 46(#13), pp. 3980-3999, 2017.
[7] C. Dab, C. Awada, A. Ruediger, "Tip-enhanced second harmonic generation: an approach for hyper-Raman spectroscopy", Plasmonics 14(#3), pp. 653-661, 2019.
[8] W. R. Zipfel, R. M. Williams, W. W. Webb, "Nonlinear magic: multiphoton microscopy in the biosciences", Nat. Biotechnol. 21(#11), pp. 1368-1376, 2003.
[9] F. Madzharova, Z. Heiner, J. Kneipp, "Surface enhanced hyper-Raman scattering of the amino acids tryptophan, histidine, phenylalanine, and tyrosine", J. Phys. Chem. C 121(#2), pp. 1235-1242, 2017.
[10] L. D. Ziegler, "Hyper-Raman spectroscopy", J. Raman Spectrosc. 21(#12), pp. 769-779, 1990.
[11] R. Shimada, H. Kano, H. O. Hamaguchi, "Hyper-Raman microspectroscopy: a new approach to completing vibrational spectral and imaging information under a microscope", Opt. Lett. 31(#3), pp. 320-322, 2006.
[12] H. Kneipp, K. Kneipp, F. Seifert, "Surface-enhanced hyper-Raman scattering (SEHRS) and surface-enhanced Raman scattering (SERS) by means of mode-locked Ti-sapphire laser excitation", Chem. Phys. Lett. 212(#3-4), pp. 374-378, 1993.
[13] D. Cialla, T. Deckert-Gaudig, C. Budich, M. Laue, R. Moller, D. Naumann, V. Deckert, J. Popp, "Raman to the limit: tip-enhanced Raman spectroscopic investigations of a single tobacco mosaic virus", J. Raman Spectrosc. 40(#3), pp. 240-243 (2009).

[14] J. D. Driskell, Y. Zhu, C. D. Kirkwood, Y. P. Zhao, R. A. Dluhy, R. A. Tripp, "Rapid and sensitive detection of rotavirus molecular signatures using surface enhanced Raman spectroscopy", PLOS ONE 5(#4), e10222 (2010).

[15] P. Hermann, A. Hermelink, V. Lausch, G. Holland, L. Moller, N. Bannert, D. Naumann, "Evaluation of tip-enhanced Raman spectroscopy for characterizing different virus strains", Analyst 136(#6), pp. 1148-1152 (2011).

[16] X. X. Han, B. Zhao, Y. Ozaki, "Label-free detection in biological applications of surface-enhanced Raman scattering", TRAC-Trend. Anal. Chem. 38, pp. 67-78 (2012).

[17] H. Sato, M. Ishigaki, A. Taketani, B. B. Andriana, "Raman spectroscopy and its use for live cell and tissue analysis", Biomed. Spectrosc. Imaging 7(#3-4), pp. 97-104 (2018).

[18] K. Moor, Y. Terada, A. Taketani, H. Matsuyoshi, K. Ohtani, H. Sato, "Early detection of virus infection in live human cells using Raman spectroscopy", J. Biomed. Opt. 23(#9), 097001 (2018).

[19] X. Zhang, X. L. Zhang, C. L. Luo, Z. Q. Liu, Y. Y. Chen, S. L. Dong, C. Z. Jiang, S. K. Yang, F. B. Wang, X. H. Xiao, "Volume-enhanced Raman scattering detection of viruses", Small 15(#11), 1805516 (2019).

[20] Y. T. Yeh, K. Gulino, Y. H. Zhanga, A. Sabestien, T. W. Chou, B. Zhou, Z. Lin, I. Albert, H. G. Lu, V. Swaminathan, E. Ghedin, M. Terrones, "A rapid and label-free platform for virus capture and identification from clinical samples", Proc. Natl. Acad. Sci. USA 117(#2), pp. 895-901 (2020).

[21] K. Olschewski, E. Kaemmer, S. Stoeckel, T. Bocklitz, T. Deckert-Gaudig, R. Zell, D. Cialla-May, K. Weber, V. Deckert, J. Popp, "A manual and an automatic TERS based virus discrimination", Nanoscale 7(#10), pp. 4545-4552 (2015).

[22] J. Y. Lim, J. S. Nam, S. E. Yang, H. Shin, Y. H. Jang, G. U. Bae, T. Kang, K. I. Lim, Y. Choi, "Identification of newly emerging influenza viruses by surface-enhanced Raman spectroscopy", Anal. Chem. 87(#23), pp. 11652-11659 (2015).

[23] V. Hoang, R. A. Tripp, P. Rota, R. A. Dluhy, "Identification of individual genotypes of measles virus using surface enhanced Raman spectroscopy", Analyst 135 (#12), pp. 3103-3109 (2010).

[24] L. Hamm, A. Gee, A. S. D. Indrasekara, "Recent advancement in the surface-enhanced Raman spectroscopy-based biosensors for infectious disease diagnosis", Appl. Sci.-Basel 9(#7), 1448 (2019).

[25] S. A. Camacho, R. G. Sobral-Filho, P. H. B. Aoki, C. J. L. Constantino, A. G. Brolo, "Zika immunoassay based on surface-enhanced Raman scattering nanoprobes", ACS Sensors 3(#3), pp. 587-594 (2018).

[26] M. Reyes, M. Piotrowski, S. K. Ang, J. Q. Chan, S. A. He, J. J. H. Chu, J. C. Y. Kah, "Exploiting the anti-aggregation of gold nanostars for rapid detection of hand, foot, and mouth disease causing enterovirus 71 using surface-enhanced Raman spectroscopy", Anal. Chem. 89(#10), pp. 5373-5381 (2017).

[27] A. M. Paul, Z. Fan, S. S. Sinha, Y. L. Shi, L. D. Le, F. W. Bai, P. C. Ray, "Bioconjugated gold nanoparticle based SERS probe for ultrasensitive identification of mosquito-borne viruses using Raman fingerprinting", J. Phys. Chem. C 119(#41), pp. 23669-23675 (2015).

[28] M. M. Joseph, N. Narayanan, J. B. Nair, V. Karunakaran, A. N. Ramya, P. T. Sujai, G. Saranya, J. S. Arya, V. M. Vijayan, K. K. Maiti, "Exploring the margins of SERS in practical domain: An emerging diagnostic modality for modern biomedical applications", Biomater. 181, pp. 140-181 (2018).

[29] X.-M. Lin, T. Deckert-Gaudig, P. Singh, M. Siegmann, S. Kupfer, Z. Zhang, S. Grafe and V. Deckert, arXiv: 1604.06598 (2016).

[30] Z. He, Z. H. Han, M. Kizer, R. J. Linhardt, X. Wang, A. M. Sinyukov, J. Z. Wang, V. Deckert, A. V. Sokolov, J. Hu, M. O. Scully, "Tip-enhanced Raman imaging of single-stranded DNA with single base resolution", J. Am. Chem. Soc. 141(#2), pp. 753-757 (2019).

[31] B. Corbett, C. Bower, A. Fecioru, M. Mooney, M. Gubbins, J. Justice, "Strategies for integration of lasers on silicon", Semicond. Sci. Tech. 28(#9), Art. 094001 (2013).

[32] X. Chen, M. M. Milosevic, S. Stankovic, S. Reynolds, T. D. Bucio, K. Li, D. J. Thomson, F. Gardes, G. T. Reed, "The emergence of silicon photonics as a flexible technology platform", Proc. IEEE 106(#12), pp. 2101-2116 (2018).

[33] T. Creazzo, E. Marchena, S. B. Krasulick, P. K. L. Yu, D. Van Orden, J. Y. Spann, C. C. Blivin, L. He, H. Cai, J. M. Dallesasse, R. J. Stone, and A. Mizrahi, "Integrated tunable CMOS laser," Opt. Express 21(#23), pp. 28048-28053 (2013).

[34] N. N. Ledentsov and V. A. Shchukin, "Novel concepts for injection lasers", Opt. Eng. 41(#12), pp. 3193-3203 (2002).

[35] M. V. Maximov, Y. M. Shernyakov, I. I. Novikov, L. Y. Karachinsky, N. Yu. Gordeev, U. Ben-Ami, D. Bortman-Arbiv, A. Sharon, V. A. Shchukin, N. N. Ledentsov, T. Kettler, K. Posilovic, D. Bimberg, "High-power low-beam divergence edge-emitting semiconductor lasers with 1- and 2-D photonic bandgap crystal waveguide", IEEE J. Sel. Topics Quantum Electorn. 14(#4), pp. 1113-1122 (2008).

[36] L. Liu, H. Qu, Y. Liu, Y. Zhang, Y. Wang, A. Qi, W. Zheng, "High-power narrow-vertical-divergence photonic band crystal laser diodes with optimized epitaxial structure", Appl. Phys. Lett. 105(#23), Art. 231110 (2014).

[37] M. J. Miah, T. Kettler, K. Posilovic, V. P. Kalosha, D. Skoczowsky, R. Rosales, D. Bimberg, J. Pohl, M. Weyers, "1.9 W continuous-wave single transverse mode emission from 1060 nm edge-emitting lasers with vertically extended lasing area", Appl. Phys. Lett. 105(#15), Art. 151105 (2014).

[38] X. L. Ma, A. J. Liu, H. W. Qu, Y. Liu, P. C. Zhao, X. J. Guo, W. H. Zheng, "Nearly diffraction-limited and low-divergence tapered lasers with photonic crystal structure", IEEE Photon. Technol. Lett. 28(#21), pp. 2403-2406 (2016).

[39] D. J. Derickson, R. J. Helkey, A. Mar, J. R. Karin, J. G. Wasserbauer, J. E. Bowers, "Short-pulse generation using multisegment mode-locked semiconductor lasers", IEEE J. Quantum Electron. 28(#10), pp. 2186-2202 (1992).

[40] D. J. Derickson, R. J. Helkey, A. Mar, J. R. Karin, J. E. Bowers, R. L. Thornton, "Suppression of multiple pulse formation in external-cavity mode-locked semiconductor lasers using intrawaveguide saturable absorbers", IEEE Photonics Technol. Lett. 4(#4), pp. 333-335 (1992).

We claim:

1. An integrated III-V/silicon or III-V/silicon nitride atomic force microscopy active optical probe comprising:
a III-V semiconductor laser chip providing a gain medium section; and a silicon or silicon nitride cantilever atomic force microscopy probe, all integrated into a single III-V/silicon or III-V/silicon nitride chip to enable, in addition to atomic force microscopy measurements, near-field optical imaging, and optical spectroscopy of the investigated sample at the nanoscale;

wherein said silicon or silicon nitride cantilever atomic force microscopy probe is a silicon or silicon nitride atomic force microscopy probe comprising a base, a cantilever, a tip formed at the end of the cantilever, and a folding mirror formed at the end of the cantilever to redirect the laser light into the tip toward the tip apex for optical excitation of the sample area located under the tip apex and for generation of optical response from that area; and wherein the III-V semiconductor laser chip is buried in the base of the silicon or silicon nitride atomic force microscopy probe right in front of the cantilever or at some distance from the cantilever and aligned with the cantilever to couple the laser light into the cantilever by way of butt or edge coupling, with the cantilever acting as an optical waveguide with silicon or silicon nitride core and air claddings.

2. The atomic force microscopy active optical probe of claim 1, wherein the tip is gold-coated and acts as an output laser mirror that reflects the laser light back into the silicon or silicon nitride cantilever/waveguide and, eventually, in the laser chip active region, thus providing a light feedback mechanism to make sure that the probe tip is supplied with intracavity high-intensity laser light.

3. The atomic force microscopy active optical probe of claim 2, wherein the III-V laser chip is fabricated from a semiconductor laser epitaxial structure incorporating longitudinal photonic band crystal waveguide and demonstrating a vertical divergence angle less than 10 degrees full width at half maximum.

4. The atomic force microscopy active optical probe of claim 3, wherein the III-V laser chip is a two-section device divided into electrically isolated gain section and saturable absorber section to allow ultrafast pulse generation.

5. The atomic force microscopy active optical probe of claim 4, wherein the saturable absorber section of the III-V laser chip is used as a photodetector for intracavity light detection.

6. The atomic force microscopy active optical probe of claim 1, wherein said silicon or silicon nitride cantilever atomic force microscopy probe, comprising a base, a cantilever, a tip formed at the end of the cantilever, and a folding mirror formed at the end of the cantilever to redirect the laser light into the tip, is produced from a specially designed silicon-on-insulator or silicon-nitride-on-insulator wafer to form a silicon or silicon nitride ridge or rib waveguide on the base of the probe and on the cantilever, and said ridge or rib waveguide is used to deliver the laser light to the probe tip shaped on top of said silicon or silicon nitride ridge or rib waveguide.

7. The atomic force microscopy active optical probe of claim 6, wherein the III-V semiconductor laser chip is buried in the base of the silicon or silicon nitride atomic force microcopy probe right in front of the silicon or silicon nitride ridge or rib waveguide and aligned with the silicon or silicon nitride ridge or rib waveguide to couple the laser light into the silicon or silicon nitride ridge or rib waveguide by way of butt or edge coupling.

8. The atomic force microscopy active optical probe of claim 7, wherein the tip is gold-coated and acts as an output laser mirror that reflects the laser light back into the silicon or silicon nitride ridge or rib waveguide and, eventually, in the laser chip active region, thus providing a light feedback mechanism to make sure that the probe tip is supplied with intracavity high-intensity laser light.

9. The atomic force microscopy active optical probe of claim 8, wherein the III-V laser chip is fabricated from a semiconductor laser epitaxial structure incorporating longitudinal photonic band crystal waveguide and demonstrating a vertical divergence angle less than 10 degrees full width at half maximum.

10. The atomic force microscopy active optical probe of claim 9, wherein the III-V laser chip is a two-section device divided into electrically isolated gain section and saturable absorber section to allow ultrafast pulse generation.

11. The atomic force microscopy active optical probe of claim 10, wherein the saturable absorber section of the III-V laser chip is used as a photodetector for intracavity light detection.

12. The atomic force microscopy active optical probe of claim 6, wherein the III-V semiconductor laser chip is evanescently coupled with the silicon or silicon nitride ridge or rib waveguide.

13. The atomic force microscopy active optical probe of claim 12, wherein the tip is gold-coated and acts as an output laser mirror that reflects the laser light back into the silicon or silicon nitride ridge or rib waveguide and, eventually in the laser chip active region, thus providing a light feedback mechanism to make sure that the probe tip is supplied with intracavity high-intensity laser light.

14. The atomic force microscopy active optical probe of claim 1, wherein the epitaxial structure of the III-V laser chip is that of quantum cascade semiconductor laser.

* * * * *